(12) United States Patent
Imanari et al.

(10) Patent No.: US 8,440,353 B2
(45) Date of Patent: May 14, 2013

(54) LITHIUM MIXED METAL OXIDE

(75) Inventors: Yuichiro Imanari, Tsukuba (JP);
Hiroshi Hamamatsu, Tsukuba (JP);
Yoshihiro Kawakami, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 547 days.

(21) Appl. No.: 12/667,158

(22) PCT Filed: Jul. 1, 2008

(86) PCT No.: PCT/JP2008/062255
§ 371 (c)(1),
(2), (4) Date: Dec. 29, 2009

(87) PCT Pub. No.: WO2009/005164
PCT Pub. Date: Jan. 8, 2009

(65) Prior Publication Data
US 2011/0059363 A1    Mar. 10, 2011

(30) Foreign Application Priority Data

Jul. 3, 2007  (JP) .................. 2007-174894
Dec. 26, 2007 (JP) .................. 2007-333993

(51) Int. Cl.
*H01M 4/13* (2010.01)
(52) U.S. Cl.
USPC ............ 429/231.95; 429/231.7; 429/224
(58) Field of Classification Search ............. 429/231.95, 429/231.7, 224
See application file for complete search history.

(56) References Cited

U.S. PATENT DOCUMENTS

| | | |
|---|---|---|
| 2006/0188780 A1 | 8/2006 | Fujii et al. |
| 2007/0026318 A1* | 2/2007 | Kishi et al. .................. 429/341 |
| 2007/0281206 A1* | 12/2007 | Fujikawa et al. ............. 429/62 |
| 2009/0011334 A1 | 1/2009 | Shizuka et al. |
| 2009/0280412 A1 | 11/2009 | Imanari et al. |

FOREIGN PATENT DOCUMENTS

| | | |
|---|---|---|
| JP | 8-037007 A | 2/1996 |
| JP | 11-102703 A | 4/1999 |
| JP | 2000100408 | 4/2000 |

(Continued)

OTHER PUBLICATIONS

Hwang et al. (Variation of chemical bonding nature of layered LiMnO2 upon delithiation/relithiation and Cr substitution, Solid State Ionics 151 (2002) 275-283).*
Supplementary European Search Report issued Dec. 14, 2011 in European Patent Application No. 08 79 0921.

(Continued)

*Primary Examiner* — Patrick Ryan
*Assistant Examiner* — Ben Lewis
(74) *Attorney, Agent, or Firm* — Sughrue Mion, PLLC

(57) ABSTRACT

A lithium mixed metal oxide containing Li, Mn and M (M represents at least one metal element, and is free from Li or Mn), and having a peak around 1.5 Å (peak A), a peak around 2.5 Å (peak B), and the value of $I_B/I_A$ is not less than 0.15 and not more than 0.9 in a radial distribution function obtained by subjecting an extended X-ray absorption fine structure (EX-AFS) spectrum at K absorption edge of Mn in the oxide to the Fourier transformation, wherein $I_A$ is the intensity of peak A and $I_B$ is the intensity of peak B.

9 Claims, 2 Drawing Sheets

FOREIGN PATENT DOCUMENTS

| | | |
|---|---|---|
| JP | 2003-346806 A | 12/2003 |
| JP | 2005-097087 A | 4/2005 |
| JP | 2006-001781 A | 1/2006 |
| JP | 2006-036620 A | 2/2006 |
| JP | 2006-117517 A | 5/2006 |
| JP | 2006-307163 A | 11/2006 |
| WO | 2006/085467 A1 | 8/2006 |
| WO | 2008/032754 A | 3/2008 |
| WO | 2008/032754 A1 | 3/2008 |

OTHER PUBLICATIONS

Won-Sub Yoon et al., "Li MAS NMR and in situ X-ray studies of lithium nickel manganese oxides", Journal of Power Sources, vol. 119-121, Jun. 1, 2003, pp. 649-653.

Seong-Ju Hwang et al., "Variation of chemical bonding nature of layered $LiMnO_2$ upon delithiation/relithiation and Cr substitution", Solid State Ionics, vol. 151, No. 1-4, Nov. 1, 2002, pp. 275-283.

* cited by examiner

LITHIUM MIXED METAL OXIDE

CROSS REFERENCE TO RELATED APPLICATIONS

This application is a National Stage of International Application No. PCT/JP2008/062255 filed Jul. 1, 2008, claiming priority based on Japanese Patent Application Nos. 2007-174894, filed Jul. 3, 2007 and 2007-333993, filed Dec. 26, 2007, the contents of all which are incorporated herein by reference in their entirety.

TECHNICAL FIELD

The present invention relates to a lithium mixed metal oxide. More particularly, the present invention relates to a lithium mixed metal oxide used as a cathode active material for non-aqueous electrolyte secondary battery.

BACKGROUND ART

A lithium mixed metal oxide is used as a cathode active material for non-aqueous electrolyte secondary batteries such as lithium secondary batteries. Lithium secondary batteries have been already put into practical use as an electrical source of cellular telephones, notebook computers and the like, and further, tried to be applied in middle size and large size applications such as an automobile application, electric power storage application and the like.

As lithium mixed metal oxides used for cathode active materials of conventional lithium secondary batteries, JP-A No. 2002-100356 (Example 6) discloses a lithium-nickel-manganese-cobalt mixed oxide, and specifically discloses $LiNi_{0.45}Mn_{0.45}Co_{0.1}O_2$ prepared by adding an alkali aqueous solution to a mixed aqueous solution of nickel sulfate, manganese sulfate and cobalt sulfate to induce co-precipitation, calcining the resultant co-precipitated hydroxide in an atmosphere at 550° C., further mixing lithium carbonate, and calcining the mixture in a nitrogen gas at 800° C.

However, as to lithium secondary batteries containing conventional cathode active material, the capacity retention in a charge and discharge cycle test is not sufficient. The present invention has an object of providing a lithium mixed metal oxide useful for non-aqueous electrolyte secondary batteries, which can show high capacity retention.

DISCLOSURE OF THE INVENTION

The present inventors have variously studied and resultantly found that a specific lithium mixed metal oxide corresponds to the above-described object, leading to completion of the present invention.

That is, the present invention provides the following.

<1> A lithium mixed metal oxide containing Li, Mn and M (M represents at least one metal element, and is free from Li or Mn), and having a peak at around 1.5 Å (peak A), a peak at around 2.5 Å (peak B), and the value of $I_B/I_A$ is not less than 0.15 and not more than 0.9 in a radial distribution function obtained by subjecting an extended X-ray absorption fine structure (EXAFS) spectrum at K absorption edge of Mn in the oxide to the Fourier transformation, wherein $I_A$ is the intensity of peak A and $I_B$ is the intensity of peak B.

<2> The lithium mixed metal oxide according to <1>, wherein M represents Co and/or Ni.

<3> The lithium mixed metal oxide according to <1> or <2>, wherein the lithium mixed metal oxide has a layered crystal structure.

<4> The lithium mixed metal oxide according to any one of <1> to <3>, wherein the amount (mol) of Mn is not less than 0.4 and not more than 1 with respect to the total amount (mol) of Mn and M.

<5> The lithium mixed metal oxide according to any one of <1> to <4>, wherein the amount (mol) of Li is not less than 1.4 and not more than 1.8 with respect to the total amount (mol) of Mn and M.

<6> A cathode active material for non-aqueous electrolyte secondary battery comprising the lithium mixed metal oxide according to any one of <1> to <5>.

<7> A cathode for non-aqueous electrolyte secondary battery comprising the cathode active material for non-aqueous electrolyte secondary battery according to <6>.

<8> A non-aqueous electrolyte secondary battery comprising the cathode for non-aqueous electrolyte secondary battery according to <7>.

<9> The non-aqueous electrolyte secondary battery according to <8>, further comprising a separator.

<10> The non-aqueous electrolyte secondary battery according to <9>, wherein the separator is a separator composed of a laminated porous film obtained by laminating a heat resistant porous layer containing a heat resistant resin and a porous film containing a thermoplastic resin.

MODES FOR CARRYING OUT THE INVENTION

Figure 1:
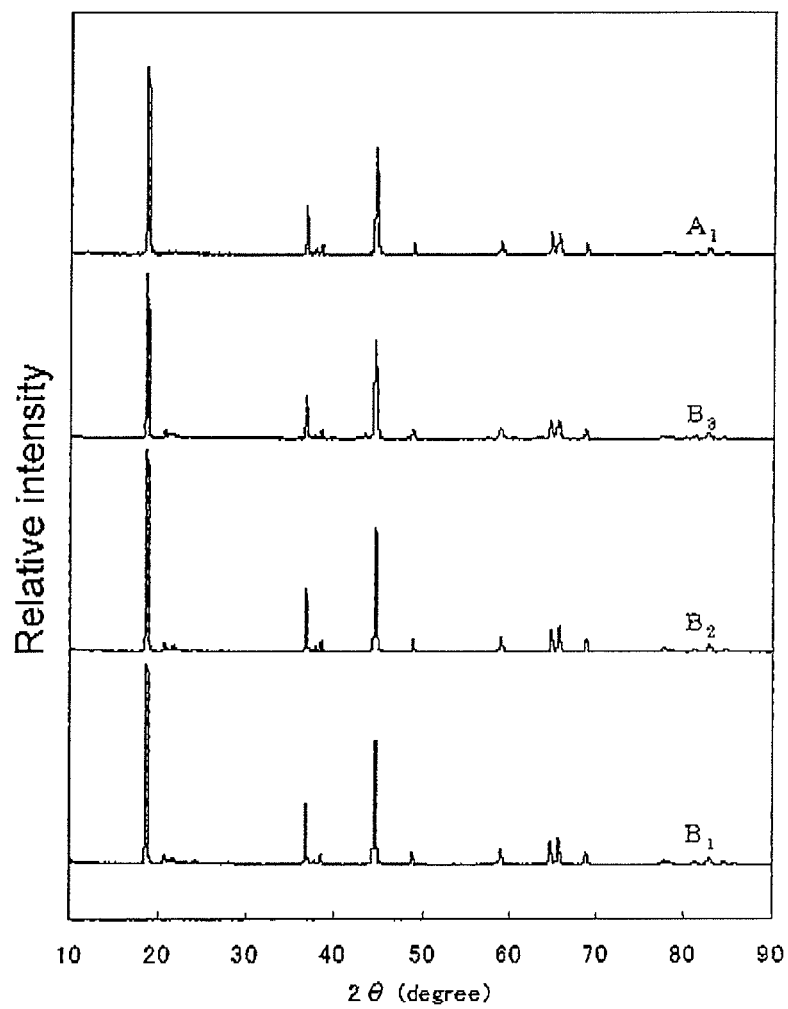
FIG. 1 shows powder X-ray diffraction patterns of powders in Examples and Comparative example.
Figure 2:
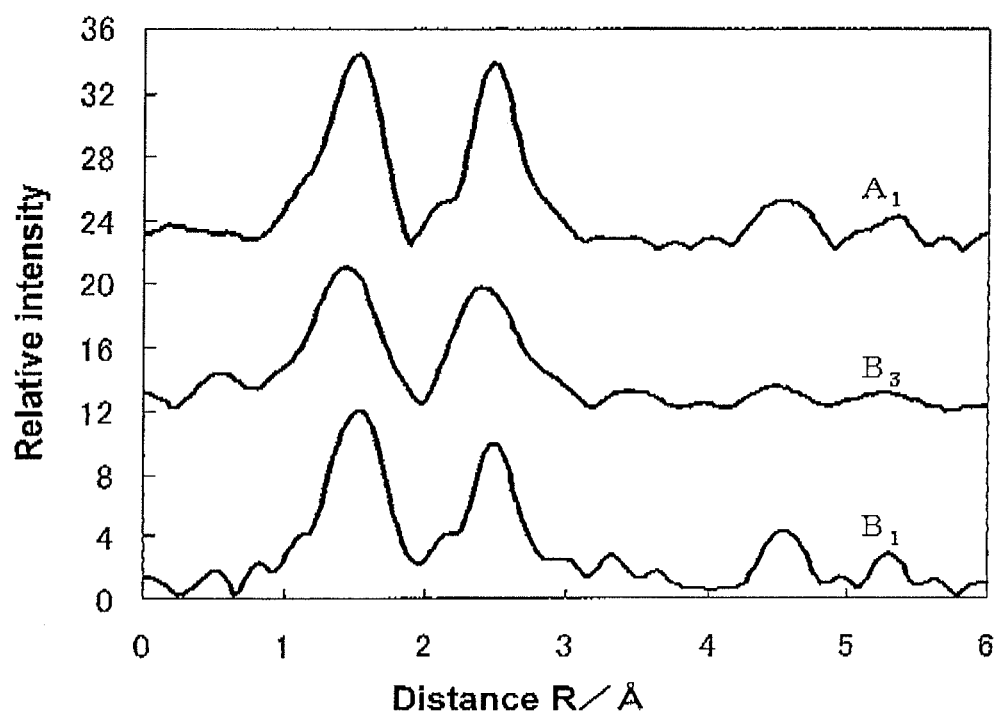
FIG. 2 shows radial distribution functions obtained from EXAFS spectra at K absorption edge of Mn of powders in Example (B1), Example (B3) and Comparative Example (A1).

The present invention provides a lithium mixed metal oxide containing Li, Mn and M (M represents at least one metal element, and is free from Li or Mn), and having a peak at around 1.5 Å (peak A), a peak at around 2.5 Å (peak B), and the value of $I_B/I_A$ is not less than 0.15 and not more than 0.9 in a radial distribution function obtained by subjecting an extended X-ray absorption fine structure (EXAFS) spectrum at K absorption edge of Mn in the oxide to the Fourier transformation, wherein $I_A$ is the intensity of peak A and $I_B$ is the intensity of peak B.

The EXAFS spectrum in the present invention will be illustrated. The EXAFS spectrum in the present invention is dealt in the same manner as for general EXAFS spectra, and the measurement and theory of the spectrum are described, for example, in "X-ray Absorption Spectral Method - - - XAFS and its application - - - " (edited by Toshiaki Ohta (2002)). Specifically, when a monochromatic X-ray is allowed to transmit through a substance, the X-ray absorbance of this substance is obtained from the intensity of the X-ray irradiated on the substance (incident X-ray intensity: $I_0$) and the intensity of the X-ray transmitted through the substance (transmitted X-ray intensity: $I_1$), and if the X-ray absorption spectrum (x axis-y axis) is measured with change of the energy of the monochromatic X-ray irradiated on the substance, namely, the energy of the incident X-ray (eV, x axis) while monitoring the X-ray absorbance (y axis), a point of steep increase in the X-ray absorbance is found, and the value of the x axis at this point is called absorption edge. The absorption edge is inherent to an element constituting the substance. In the X-ray absorption spectrum, a fine vibration structure appearing in a region on the energy side higher by about 20 to 1000 eV than this absorption edge is called an extended X-ray absorption fine structure (EXAFS), and its spectrum is called an EXAFS spectrum.

When the Fourier transformation is carried out on the EXAFS spectrum, a radial distribution function with an X-ray absorbing atom (atom to be noticed) as a center is obtained. By this radial distribution function, information such as a distance between the X-ray absorbing atom and an X-ray scattering atom (atom around the X-ray absorbing atom), the number of X-ray scattering atoms, and the like can be obtained, and information around the atom to be noticed can be obtained. In the present invention, the K absorption edge of Mn is paid to attention.

The lithium mixed metal oxide in the present invention is a lithium mixed metal oxide containing Li, Mn and M (M represents at least one metal element and is free from Li or Mn), and having a peak around 1.5 Å (peak A), a peak around 2.5 Å (peak B), and the value of $I_B/I_A$ is not less than 0.15 and not more than 0.9 in a radial distribution function obtained by subjecting an extended X-ray absorption fine structure (EXAFS) spectrum at K absorption edge of Mn in the oxide to the Fourier transformation, wherein $I_A$ is the intensity of peak A and $I_B$ is the intensity of peak B. A non-aqueous electrolyte secondary battery comprises the oxide and has improved capacity retention. The value of $I_B/I_A$ is preferably in the range of not less than 0.3 and not more than 0.9, more preferably in the range of not less than 0.7 and not more than 0.9, and in this range, the capacity retention is further improved.

In the radial distribution function in the present invention, the peak A is ascribable to O (oxygen atom) connected to the Mn atom to be noticed in the lithium mixed metal oxide, and appears usually at not less than 1.4 Å and not more than 1.9 Å, preferably at not less than 1.5 Å and not more than 1.6 Å. The peak B is ascribable to an atom X adjacent to the Mn atom to be noticed (here, X represents a metal atom, for example, Li, Mn, Ni, Co, Fe and the like), and appears usually at not less than 2.44 Å and not more than 2.50 Å, preferably at not less than 2.46 Å and not more than 2.50 Å.

In the present invention, the number of X atoms adjacent to Mn is usually not less than 3 and not more than 6.

The number of O atoms connected to Mn is usually not less than 4 and not more than 6.

It is preferable that the lithium mixed metal oxide of the present invention has a layered crystal structure, and it is more preferable from the standpoint of the discharge capacity of the resultant non-aqueous electrolyte secondary battery that the oxide has a crystal structured belonging to a space group R-3m or C2/m. The space group R-3m is included in a crystal structure of hexagonal crystal form, and the crystal structure of hexagonal crystal form belongs to any one space group selected from P3, $P3_1$, $P3_2$, R3, P-3, R-3, P312, P321, $P3_1 12$, $P3_1 21$, $P3_2 12$, $P3_2 21$, R32, P3m1, P31m, P3c1, P31c, R3m, R3c, P-31m, P-31c, P-3m1, P-3c1, R-3m, R-3c, P6, $P6_1$, $P6_5$, $P6_2$, $P6_4$, $P6_3$, P-6, P6/m, $P6_3/m$, P622, $P6_1 22$, $P6_5 22$, $P6_2 22$, $P6_4 22$, $P6_3 22$, P6mm, P6cc, $P6_3 cm$, $P6_3 mc$, P-6m2, P-6c2, P-62m, P-62c, P6/mmm, P6/mcc, $P6_3/mcm$ and $P6_3/mmc$. The space group C2/m is included in a crystal structure of monoclinic crystal form, and the crystal structure of monoclinic crystal form belongs to any one space group selected from P2, $P2_1$, C2, Pm, Pc, Cm, Cc, P2/m, $P2_1/m$, C2/m, P2/c, $P2_1/c$ and C2/c.

The space group can be confirmed according to the following. First, a lithium mixed metal oxide is subjected to powder X-ray diffraction measurement using CuKα as a radiation source and in which the measurement range of diffraction angle 2θ is not less than 10° and not more than 90°, then, based on the result, the Rietveld analysis is carried out to determine the crystal structure of the lithium mixed metal oxide and a space group of the crystal structure. The Rietveld analysis is a method for analyzing the crystal structure of a material using data of a diffraction peak in the powder X-ray diffraction measurement of the material (diffraction peak intensity, diffraction angle 2θ), and is a conventional technique (see, e.g., "Practice of Powder X-ray Analysis—Rietveld method approach—", published on Feb. 10, 2002, edited by X-ray Analytical Study Conference, The Japan Society for Analytical Chemistry).

Regarding the formulation of Li, Mn and M in the present invention, the amount (mol) of Li with respect to the total amount (mol) of Mn and M is usually more than 1.0 and less than 2.0, and from the standpoint of further enhancement of the capacity retention, it is preferably not less than 1.4 and not more than 1.8, more preferably not less than 1.5 and not more than 1.7. Even if the amount (mol) of Li in the lithium mixed metal oxide of the present invention is in the above-described range, the amount (mol) of Li decreases in some cases when a non-aqueous electrolyte secondary battery is produced using the oxide as a cathode active material and charge and discharge are repeated. Also in this case, the value of $I_B/I_A$ is within the above-described range.

In the present invention, regarding the formulation of Mn and M, the amount (mol) of Mn with respect to the total amount (mol) of Mn and M is preferably in the range of not less than 0.4 and not more than 1, more preferably not less than 0.4 and not more than 0.9, further preferably not less than 0.4 and not more than 0.8, from the standpoint of the discharge capacity of the resultant non-aqueous electrolyte secondary battery.

In the present invention, it is preferable from the standpoint of further enhancement of the effect that M represents at least one element selected from the group consisting of Co, Ni, and Fe, and further, it is more preferable from the standpoint of the discharge capacity of the resultant non-aqueous electrolyte secondary battery that M represents Co and/or Ni.

In the present invention, when M represents Co and/or Ni, the amount (mol) of Co with respect to the total amount (mol) of Co and Ni is preferably not less than 0 and not more than 0.4 from the standpoint of a capability of further increasing the capacity retention, and it is more preferably not less than 0 and not more than 0.35, further preferably not less than 0 and not more than 0.25.

The lithium mixed metal oxide of the present invention is usually in the form of powder, and has a BET specific surface area of usually about not less than 1 m²/g and not more than 30 m²/g. For obtaining a non-aqueous electrolyte secondary battery showing higher output under high electric current rate, the lithium mixed metal oxide has a BET specific surface area of preferably not less than 2 m²/g and not more than 20 m²/g, more preferably not less than 3 m²/g and not more than 16 m²/g.

The lithium mixed metal oxide of the present invention may be subjected to surface treatments such as coating the surface of the lithium mixed metal oxide particles used as a core material with a compound containing at least one element selected from the group consisting of B, Al, Ga, In, Si, Ge, Sn, Mg and transition metal elements. Among these elements at least one element selected from the group consisting of B, Al, Mg, Co, Cr and Mn is preferable, and Al is more preferable from the standpoint of operability. Examples of the compound include oxides, fluorides, sulfides, hydroxides, oxyhydroxides, carbonates, nitrates and organic acid salts of the elements, or mixtures thereof. Of them, oxides, hydroxides and oxyhydroxides or mixtures thereof are preferable. Among the compounds, alumina is more preferable.

Next, a method for producing the lithium mixed metal oxide of the present invention will be illustrated with examples in which M represents Co and Ni.

The lithium mixed metal oxide of the present invention can be produced by a method of calcining a metal compound mixture which can be converted into a lithium mixed metal oxide of the present invention by calcination, namely, a solid phase reaction. Specifically, when the molar ratio of Li:Ni:Mn:Co is 1:x:y:z in the formulation of the lithium mixed metal oxide of the present invention, it can be obtained by weighing and mixing a compound containing Li, a compound containing Ni, a compound containing Mn and a compound containing Co so that the molar ratio of Li:Ni:Mn:Co is A:x:y:z (wherein, A represents a value in the range of not less than 2 and not more than 5), then, calcining the resultant metal compound mixture in the temperature range of preferably from 800° C. to 1000° C. It is preferable that A represents a value in the range of not less than 2.1 and not more than 3.5.

As the compound containing metal elements of Li, Ni, Mn and Co, oxides are used, or there can be used hydroxides, oxyhydroxides, carbonates, nitrates, acetates, halides, oxalates, alkoxides and the like which can be decomposed and/or oxidized at high temperatures to become oxides. Of them, preferable as the compound containing Li are hydroxides and/or carbonates, preferable as the compound containing Ni are hydroxides and/or oxides, preferable as the compound containing Mn are carbonates and/or oxides, and preferable as the compound containing Co are oxides and/or hydroxides. Further, a compound containing two or more of the metal elements may also be used as the compound containing a metal element.

For enhancing the crystallinity of the lithium mixed metal oxide thereby increasing the initial discharge capacity, the metal compound mixture before calcination may further contain a compound containing boron. The content of the compound containing boron is usually not less than 0.00001 mol % and not more than 5 mol % in terms of boron, preferably not less than 0.0001 mol % and not more than 3 mol % in terms of boron, with respect to the total mole of metal elements excluding lithium in the metal compound mixture. Examples of the compound containing boron include boron oxide and boric acid, preferably boric acid. Boron further contained in the metal compound mixture may remain in the lithium mixed metal oxide of the present invention after calcination, or may be removed by washing, evaporation and the like.

Mixing of the compounds containing a metal element may be carried out in dry mode or wet mode, and preferable is simpler dry mode mixing. Examples of the dry mode mixer include a V-shaped mixer, a W-shaped mixer, ribbon mixer, drum mixer, and dry ball mill.

A lithium mixed metal oxide is obtained by calcining the metal compound mixture in the temperature range of not lower than 800° C. and not higher than 1000° C. for 2 to 30 hours, optionally following compression molding the metal compound mixture. As the calcination atmosphere, air, oxygen, nitrogen, argon or mixed gases thereof can be used, and an atmosphere containing oxygen is preferable.

The lithium mixed metal oxide of the present invention can be produced also by, for example, the following hydrothermal reaction method, namely, a production method comprising the following steps (1), (2), (3), (4) and (5) in this order, in addition to the solid phase reaction.

(1) mixing an aqueous solution containing Mn and M, and an alkali (A) to form a precipitate.

(2) hydrothermally treating a liquid mixture containing the precipitate and an oxidizer, and an alkali (B) containing LiOH in the temperature range of 150° C. to 350° C. to obtain a hydrothermally treated article.

(3) washing the hydrothermally treated article to obtain a washed article.

(4) drying the washed article to obtain a dried article.

(5) mixing the dried article and a lithium compound in dry mode mixing, and calcining the resultant mixture to obtain a calcined article.

The aqueous solution containing Mn and M in the step (1) may be an aqueous solution containing Mn and M. When a water-soluble compound containing Mn and M such as a chloride, nitrate, sulfate, oxalate, and acetate is used as the raw material, it may be advantageous that the aqueous solution is prepared by dissolving the compound in water. The water-soluble compounds may be anhydrides or hydrates. For example, when M represents Co and/or Ni, $Co(NO_3)_2.6H_2O$ may be used as the compound containing Co, and $Ni(NO_3)_2.6H_2O$ may be used as the compound containing Ni. As the compound containing Mn, $MnCl_2.4H_2O$ may be used. When a metal material containing Mn and M, or a compound containing Mn and M with low dissolvability in water such as a hydroxide, acid hydroxide, and oxide is used as the raw material, it may be advantageous that the aqueous solution is prepared by dissolving them in an acid such as hydrochloric acid. For Ni and M, two or more compounds among the water-soluble compounds, the compounds with low dissolvability in water, and the metal materials may be used together.

As the alkali (A) in the step (1), there can be used at least one anhydride and/or at least one hydrate of a compound selected from the group consisting of LiOH (lithium hydroxide), NaOH (sodium hydroxide), KOH (potassium hydroxide), $NH_3$ (ammonia), $Na_2CO_3$ (sodium carbonate), $K_2CO_3$ (potassium carbonate) and $(NH_4)_2CO_3$ (ammonium carbonate), and usually, these are dissolved in water to give an aqueous solution to be used. The concentration of the alkali (A) in the aqueous solution is usually about 0.1 to 20 M, preferably about 0.5 to 10 M. From the standpoint of decreasing impurities in the lithium mixed metal oxide, it is preferable to use an anhydride and/or hydrate of LiOH as the alkali (A). From the standpoint of production cost, it is preferable to use an anhydride and/or hydrate of KOH as the alkali (A). Two or more of these alkalis (A) may be used together.

In mixing the aqueous solution containing Mn and M and the alkali (A) to form a precipitate in the step (1), for example, an aqueous solution containing prescribed concentrations of Mn and M is added in prescribed amount to an aqueous solution of the alkali (A) of prescribed concentration. For obtaining a precipitate with uniform particle size, it is more preferable that an aqueous solution containing Mn and M is dropped while stirring an aqueous solution of the alkali (A). In the method, measurement of pH of the aqueous solution is initiated while stirring the aqueous solution of the alkali (A). There is a tendency of lowering of the measured pH with dropping of the aqueous solution containing Mn and M, and in the step (1), it is preferable that the measured pH is not less than 11.

From the standpoint of inducing uniform precipitation, the aqueous solution containing Mn and M and/or the aqueous solution of the alkali (A) may be cooled and used. The cooling temperature is preferably not higher than 10° C., more preferably about not lower than −15° C. and not higher than 5° C. When the cooling temperature is not higher than 0° C., addition to the aqueous solution containing Mn and M and/or the aqueous solution of the alkali (A) may be carried out at a proportion of 1 to 50 parts by weight of an anti-freeze liquid such as methanol, ethanol, and ethylene glycol with respect to 100 parts by weight of water.

From the standpoint of further enhancing the effect of the present invention, the aqueous solution containing Mn and M may be added into the aqueous solution of the alkali (A) while conducting an operation of introducing an oxygen-containing gas such as air. When the aqueous solution of the alkali (A) is added to the aqueous solution containing Mn and M, it is preferable to carry out an operation of introducing the gas into the aqueous solution containing Mn and M. After mixing, an operation of introducing the gas may be carried out. The operation time is about 1 hour to 5 days, and the operation temperature is about 0 to 100° C.

When a mixed liquid having the precipitate formed by mixing in the step (1) is subjected to solid-liquid separation such as filtration, the precipitate obtained from the mixed liquid by solid-liquid separation is dispersed again in water to obtain a dispersion liquid which is used in the step (2). The precipitate obtained by solid-liquid separation may be subjected to washing. The mixed liquid having the precipitate may be used as it is in the step (2) without solid-liquid separation.

In the step (2), the liquid mixture contains the precipitate obtained in the step (1), an oxidizer and an alkali (B) containing LiOH. The oxidizer is used for oxidizing a metal element in the liquid mixture. The oxidizer is, for example, at least one selected from the group consisting of NaClO (sodium hypochlorite), $HNO_3$ (nitric acid), $KClO_3$ (potassium chlorate) and $H_2O_2$ (hydrogen peroxide), and $H_2O_2$ and/or $KClO_3$ is preferable from the standpoint of production cost and oxidation reactivity, and $KClO_3$ is more preferable from the standpoint of easier control of the oxidation reaction. The alkali (B) containing LiOH may be an anhydride and/or hydrate of LiOH, or may further contain an anhydride and/or hydrate of NaOH and an anhydride and/or hydrate of KOH, preferably an anhydride and/or hydrate of KOH, in addition to the anhydride and/or hydrate of LiOH. These oxidizers and alkalis (B) can be added to the mixed liquid or dispersion liquid to prepare a liquid mixture. The concentration of the oxidizer in the liquid mixture is usually about 0.1 to 10 M, preferably about 0.3 to 5 M, and the concentration of the alkali (B) in the liquid mixture is usually about 0.1 to 30 M, preferably about 1 to 20 M, and the content of the precipitate in the liquid mixture is usually about 1 to 200 g/(1 L of liquid mixture). The concentration of Li in the liquid mixture is preferably 0.1 to 10 M, more preferably 0.5 to 5 M. The liquid mixture contain optionally lithium chloride, lithium nitrate or lithium carbonate. The liquid mixture has pH of preferably not less than 11, more preferably not less than 13 to accelerate the reaction in the hydrothermal treatment.

In the step (2), the liquid mixture is hydrothermally treated in the temperature range of 150° C. to 350° C. to obtain a hydrothermally treated article. The pressure in this temperature range is usually about 0.4 MPa to 17 MPa. As the hydrothermal treatment apparatus, an autoclave may be advantageously used (those made of materials excellent in heat resistance and corrosion resistance such as stainless steel, Inconel (registered trademark), and Hastelloy (registered trademark) can be preferably used). The preferable temperature of the hydrothermal treatment temperature is from 180° C. to 250° C. The time of the hydrothermal treatment is usually from about 0.1 to 150 hours, preferably from 0.5 to 50 hours.

In the step (3), the hydrothermally treated article is washed. By washing, impurities such as lithium hydroxide, lithium chloride, lithium nitrate, lithium carbonate, and oxidizers in the hydrothermally treated article can be removed. In the washing, usually, the hydrothermally treated article is subjected to filtration and the like to induce solid-liquid separation, and the resultant solid content is washed with water, water-alcohol, or acetone, and is subjected to solid-liquid separation again. The solid content after solid-liquid separation is the washed article.

In the step (4), the washed article is dried to obtain a dried article. Drying is usually carried out by a thermal treatment, and it may also be carried out by blast drying, vacuum drying and the like. In drying by a thermal treatment, it is carried out usually at 50 to 300° C., preferably at about 100° C. to 200° C.

In the step (5), the dried article and a lithium compound are mixed by dry mode mixing to obtain a mixture, and the mixture is calcined to obtain a calcined article. The calcined article is a lithium mixed metal oxide of the present invention. The lithium compound in the step (5) is, for example, at least one anhydride and/or at least one hydrate of a compound selected from the group consisting lithium hydroxide, lithium chloride, lithium nitrate and lithium carbonate, preferably at least one anhydride and/or at least one hydrate of a compound selected from the group consisting lithium hydroxide and lithium carbonate. It is necessary that the lithium compound is in solid condition. Mixing of the dried article and the lithium compound is carried out by dry mode mixing. It is preferable to mix 50 to 300 parts by weight of the lithium compound with respect to 100 parts by weight of the dried article. Examples of the mixing apparatus include a stirring mixer, a V-shaped mixer, a W-shaped mixer, a ribbon mixer, a drum mixer, and a ball mill.

In the step (5), the calcination temperature is preferably not lower than 300° C. and not higher than 1000° C., more preferably not lower than 500° C. and not higher than 900° C. The retention time at the calcination temperature is usually 0.1 to 20 hours, preferably 0.5 to 8 hours. The temperature rising rate up to the calcination temperature is usually 50° C. to 400° C./hour, and the temperature dropping rate from the calcination temperature down to room temperature is usually 10° C. to 400° C./hour. As the calcination atmosphere, air, oxygen, nitrogen, argon or mixed gases thereof can be used, and preferable is an atmosphere containing oxygen.

The lithium mixed metal oxide obtained by the solid phase reaction and hydrothermal reaction described above may be ground using a ball mill, jet mill or the like, and grinding and calcination may be repeated twice or more. The resultant lithium mixed metal oxide can be optionally washed or classified.

The lithium mixed metal oxide of the present invention obtained as described above can be used singularly as a cathode active material for non-aqueous electrolyte secondary battery. Further, the lithium mixed metal oxide of the present invention subjected to a surface treatment for coating with the compound can be used as a cathode active material for non-aqueous electrolyte secondary battery.

Next, the cathode for non-aqueous electrolyte secondary battery comprising the cathode active material for non-aqueous electrolyte secondary battery of the present invention will be illustrated.

The cathode for non-aqueous electrolyte secondary battery is produced by coating a cathode collector with a cathode mixture containing a cathode active material, an electrical conductive material and a binder. As the electrical conductive material, carbonaceous materials can be used. Examples of the carbonaceous material include a graphite powder, carbon black, acetylene black, and fibrous carbon material. Since carbon black and acetylene black are fine particles and have large surface area, they can be added in small amount into a cathode mixture to enhance the electrical conductivity in the cathode thereby improving charge and discharge efficiency and rate property. When added in too large amount, adhesion between the cathode mixture and the cathode collector with the binder is lowered, thereby rather causing an increase in the internal resistance. Usually, the proportion of the electric conductive material in the cathode mix is not less than 5 parts by weight and not more than 20 parts by weight with respect to 100 parts by weight of the cathode active material. When a fibrous carbon material such as graphitized carbon fiber, and carbon nano-tube is used as the electrical conductive material, the proportion can also be lowered.

As the binder, thermoplastic resins can be used. Examples of the binder include fluorine resins such as polyvinylidene fluoride (hereinafter, referred to as PVdF in some cases), polytetrafluoroethylene (hereinafter, referred to as PTFE in some cases), ethylene tetrafluoride•propylene hexafluoride•vinylidene fluoride copolymer, propylene hexafluoride•vinylidene fluoride copolymer, ethylene tetrafluoride•perfluorovinyl ether copolymer and the like, polyolefin resins such as polyethylene, polypropylene and the like, and other resins. These resins may be used in combination with another or more. When a fluorine resin and a polyolefin resin are used as the binder and contained so that the proportion of the fluorine resin is 1 to 10 wt % and the proportion of the polyolefin resin is 0.1 to 2 wt % with respect to the cathode mix, cathode mix excellent in adhesion to a cathode collector can be obtained.

As the cathode collector, Al, Ni, stainless steel or the like can be used, and Al is preferable since it can be processed easily into a thin membrane and it is cheap. The method for coating a cathode collector with a cathode mixture is, for example, a pressure molding, or a method in which a cathode mixture is formed into a paste using an organic solvent and the like, and applied on a cathode collector and dried, then, pressed or the like to attain fixation. When formed into a paste, a slurry composed of a cathode active material, an electrical conductive material, a binder and an organic solvent is prepared. Examples of the organic solvent include amine solvents such as N,N-dimethylaminopropylamine, and diethylenetriamine, ether solvents such as tetrahydrofuran, ketone solvents such as methyl ethyl ketone, ester solvent such as methyl acetate and, amide solvents such as dimethylacetamide, and N-methyl-2-pyrrolidone, and other solvents.

Examples of the method of applying a cathode mixture on a cathode collector include a slit die coating, screen coating, curtain coating, knife coating, gravure coating, and electrostatic spraying. By the methods, a cathode for non-aqueous electrolyte secondary battery can be produced.

Using the cathode for non-aqueous electrolyte secondary battery, a non-aqueous electrolyte secondary battery can be produced as described below. That is, a separator, an anode and the cathode are laminated and wound to obtain an electrode group. The electrode group is accommodated in a battery case, and then impregnated with an electrolytic solution composed of an organic solvent containing an electrolyte to produce a non-aqueous electrolyte secondary battery.

The electrode group is, for example, in the form with the cross-sectional shape of circle, ellipse, rectangle, or rounded rectangle when cut along a direction vertical to the winding axis. The battery ism for example, in the form of paper, coin, cylinder, or square.

The anode may advantageously be a material capable of doping and releasing lithium ions with lower potential than the cathode, and is, for example, an electrode in which an anode collector is coated with anode mixture containing an anode material, or electrodes made solely of an anode material. The anode material is a material capable of doping and releasing lithium ions with lower potential than the cathode, and examples thereof include carbonaceous materials, chalcogen compounds (oxides, sulfides and the like), nitrides, metals or alloys. These anode materials may be used in combination with another or more.

The anode materials will be illustrated below. Examples of the carbonaceous material include graphites such as natural graphite and artificial graphite, cokes, carbon black, pyrolytic carbons, carbon fiber, and organic polymer compound calcined materials. Examples of the oxide include silicon oxides represented by the formula $SiO_x$ (wherein, x represents a positive actual number) such as $SiO_2$ and SiO, titanium oxides represented by the formula $TiO_x$ (wherein, x represents a positive actual number) such as $TiO_2$ and TiO, vanadium oxides represented by the formula $VO_x$ (wherein, x represents a positive actual number) such as $V_2O_5$ and $VO_2$, iron oxides represented by the formula $FeO_x$ (wherein, x represents a positive actual number) such as $Fe_3O_4$, $Fe_2O_3$, and FeO, tin oxides represented by the formula $SnO_x$ (wherein, x represents a positive actual number) such as $SnO_2$ and SnO, tungsten oxides represented by the formula $WO_x$ (wherein, x represents a positive actual number) such as $WO_3$ and $WO_2$, mixed metal oxides containing lithium and titanium and/or vanadium such as $Li_4Ti_5O_{12}$ and $LiVO_2$ (for example, $Li_{1.1}V_{0.9}O_2$). Examples of the sulfide include titanium sulfides represented by the formula $TiS_x$ (wherein, x represents a positive actual number) such as $Ti_2S_3$, $TiS_2$, and TiS, vanadium sulfides represented by the formula $VS_x$ (wherein, x represents a positive actual number) such as $V_3S_4$, $VS_2$, and VS, iron sulfides represented by the formula $FeS_x$ (wherein, x represents a positive actual number) such as $Fe_3S_4$, $FeS_2$, and FeS, molybdenum sulfides represented by the formula $MoS_x$ (wherein, x represents a positive actual number) such as $Mo_2S_3$ and $MoS_2$, tin sulfides represented by the formula $SnS_x$ (wherein, x represents a positive actual number) such as $SnS_2$ and SnS, tungsten sulfides represented by the formula $WS_x$ (wherein, x represents a positive actual number) such as $WS_2$, antimony sulfides represented by the formula $SbS_x$ (wherein, x represents a positive actual number) such as $Sb_2S_3$, selenium sulfides represented by the formula $SeS_x$ (wherein, x represents a positive actual number) such as $Se_5S_3$, $SeS_2$, and SeS. Examples of the nitride include lithium-containing nitrides such as $Li_3N$, $Li_{3-x}A_xN$ (wherein, A represents Ni and/or Co, 0<x<3). These carbonaceous materials, oxides, sulfides and nitrides may be used together, and may be any of crystalline or amorphous. An anode collector is coated with the carbonaceous materials, oxides, sulfides or nitrides to form an electrode.

Examples of the metal include lithium metal, silicon metal and tin metal. Examples of the alloy include lithium alloys such as Li—Al, Li—Ni, and Li—Si, silicon alloys such as Si—Zn, and tin alloys such as Sn—Mn, Sn—Co, Sn—Ni, Sn—Cu, and Sn—La, and additionally, also alloys such as $Cu_2Sb$, and $La_3Ni_2Sn_7$. These metals and alloys are used singularly as an electrode (for example, used in the form of foil).

Among the anode materials, carbonaceous materials composed of graphite such as natural graphite, and artificial graphite as the main component are preferably used from the standpoint of higher potential flatness, lower average discharge potential, excellent cycling property and the like. The form of the carbonaceous material may be any of a flake such as natural graphite, a sphere such as mesocarbon microbeads, a fiber such as graphitized carbon fiber, an aggregate of fine powder.

The anode mix may contain optionally a binder. The binder is, for example, a thermoplastic resin. Examples of the thermoplastic resin include PVdF, thermoplastic polyimides, carboxymethylcellulose, polyethylene, and polypropylene.

When an electrolytic solution has no ethylene carbonate described later, use of an anode mixture containing polyethylene carbonate improves the cycling property and large current discharge property of the resultant battery in some cases.

Examples of the anode collector include Cu, Ni, and stainless steel, and Cu may be advantageously used from the standpoint of a low tendency of formation of an alloy with lithium, and easiness of processing into a thin membrane. The method of coating the anode collector with the anode mixture is the same as the cathode. Examples thereof include a pressure molding, and a method in which an anode mix is formed into a paste using an organic solvent and the like and applied on an anode collector and dried, then, pressed and compressed.

The separator composes of a material in the form of porous film, non-woven fabric, woven fabric and the like. Examples of the material include a polyolefin resin such as polyethylene, and polypropylene, a fluorine resin, a nitrogen-containing and aromatic polymer. Two or more materials may be used to give the separator, and the materials may be laminated. The separator is disclosed, for example, in JP-A Nos. 2000-30686 and 10-324758, and the like. It is preferable that the thickness of the separator is as thin as possible providing that mechanical strength is kept, from the standpoint of increase in the volume energy density of the battery and decrease in the internal resistance. The separator has a thickness of usually from about 5 to 200 μm, preferably from about 5 to 40 μm.

The separator preferably has a heat resistant porous layer containing a heat resistant resin, and preferably has a porous film containing a thermoplastic resin. In a non-aqueous electrolyte secondary battery, it is usually important that, in flowing of abnormal current in a battery caused by short circuit between a cathode and an anode and the like, the current is interrupted to block excess current flow (shut down). Thus, it is required for the separator that in excess of usual use temperature, shut down is carried out at a temperature of as low as possible (when the separator has a porous film containing a thermoplastic resin, fine pores of the porous film are occluded), and that even if the temperature in the battery increases up to a certain high temperature after performing shut down, the membrane is not broken at this temperature and the condition of shut down is maintained, in other words, it is required to have high heat resistance. By using a separator composed of a laminated porous film obtained by laminating a heat resistance porous layer containing a heat resistant resin and a porous film containing a thermoplastic resin as the separator, thermal membrane breakage can be prevented effectively. The heat resistant porous layer may be laminated on one surface of the porous film, or may be laminate on both surfaces of the porous film.

The separator composed of a laminated porous film obtained by laminating a heat resistance porous layer containing a heat resistant resin and a porous film containing a thermoplastic resin will be illustrated below. The separator has a thickness of usually not more than 40 μm, preferably not more than 20 μm. When the thickness of the heat resistant porous layer is represented by A (μm) and the thickness of the porous film is represented by C (μm), the value of A/B is preferably not less than 0.1 and not more than 1. Further, from the standpoint of ion transmission, this separator has an air permeability according to the Gurley method of preferably 50 to 300 sec/100 cc, more preferably 50 to 200 sec/100 cc. This separator has a gap ratio of usually 30 to 80 vol %, preferably 40 to 70 vol %.

In the laminated porous film, the heat resistant porous layer contains a heat resistant resin. For further enhancing ion transmission, it is preferable that the thickness of the heat resistant porous layer is as thin as possible providing that mechanical strength and the like are not deteriorated, and it is preferably not less than 1 μm and not more than 10 μm, more preferably not less than 1 μm and not more than 5 μm, further preferably not less than 1 μm and not more than 4 μm. The heat resistant porous layer has fine pores, and the size (diameter) of the pore is usually not more than 3 μm, preferably not more than 1 μm.

Examples of the heat resistant resin contained in the heat resistant porous layer include polyamide, polyimide, polyamideimide, polycarbonate, polyacetal, polysulfone, polyphenylene sulfide, polyether ketone, aromatic polyester, polyether sulfone and polyether imide, and from the standpoint of further enhancing heat resistance, preferable are polyamide, polyimide, polyamideimide, polyether sulfone and polyether imide, more preferable are polyamide, polyimide and polyamideimide. Further preferably, the heat resistant resin is a nitrogen-containing aromatic polymer such as aromatic polyamide (para-oriented aromatic polyamide, meta-oriented aromatic polyamide), aromatic polyimide, aromatic polyamideimide and the like, particularly preferable is an aromatic polyamide, and from the standpoint of production, a para-oriented aromatic polyamide (hereinafter, referred to as "para-amide" in some cases) is particularly preferable. Examples of the heat resistant resin include also poly-4-methylpentene-1, and cyclic olefin polymers. Use of these heat resistant resins can enhance heat resistance, that is, the thermal membrane breakage temperature.

The thermal membrane breakage temperature is usually not lower than 160° C., depending on the kind of the heat resistant resin. Use of the nitrogen-containing aromatic polymer as the heat resistant resin can enhance the thermal membrane breakage temperature up to at most about 400° C. Use of poly-4-methylpentene-1 can enhance the thermal membrane breakage temperature up to at most about 250° C. Use of the cyclic olefin resin can enhance the thermal membrane breakage temperature up to at most about 300° C.

The para-aramide is obtained by condensation polymerization of a para-oriented aromatic diamine and a para-oriented aromatic dicarboxylic halide, and composed substantially of repeating units linked via an amide bond at a para-location of an aromatic ring or at the correspondent orientation location (for example, orientation location extending parallel or concentrically toward the reverse direction such as in 4,4'-biphenylene, 1,5-naphthalene, 2,6-naphthalene and the like). The para-amide has a para-orientation structure or the correspondent structure, and examples of The para-amide include poly(para-phenylene terephthalamide), poly(para-benzamide), poly(4,4'-benzanilide terephthalamide), poly(para-phenylene-4,4'-biphenylenedicarboxyclic amide), poly(para-phenylene-2,6-naphthalenedicarboxylic amide), poly(2-chloro-para-phenylene terephthalamide), and para-phenylene terephthalamide/2,6-dichloropara-phenylene terephthalamide copolymer.

The aromatic polyimide is preferably a wholly aromatic polyimide produced by condensation polymerization of an aromatic diacid anhydride and a diamine. Examples of the diacid anhydride include pyromellitic dianhydride, 3,3',4,4'-diphenylsulfone tetracarboxylic dianhydride, 3,3',4,4'-benzophenone tetracarboxylic dianhydride, 2,2'-bis(3,4-dicarboxyphenyl)hexafluoropropane, and 3,3',4,4'-biphenyl tetracarboxylic dianhydride. Examples of the diamine include oxydianiline, para-phenylenediamine, benzophenonediamine, 3,3'-methylenedianiline, 3,3'-diaminobenzophenone, 3,3'-diaminodiphenylsulfone, and 1,5'-naphthalenediamine. Polyimides soluble in a solvent can be suitably used. Examples of the polyimide include a polycondensate of 3,3',4,4'-diphenylsulfone tetracarboxylic dianhydride and an aromatic diamine.

The aromatic polyamideimide is obtained by, for example, condensation polymerization of an aromatic dicarboxylic acid and an aromatic diisocyanate, or condensation polymerization of an aromatic diacid anhydride and an aromatic diisocyanate. Examples of the aromatic dicarboxylic acid include isophthalic acid, and terephthalic acid. Examples of the aromatic diacid anhydride include trimellitic anhydride. Examples of the aromatic diisocyanate include 4,4'-diphenylmethane diisocyanate, 2,4-tolylene diisocyanate, 2,6-tolylene diisocyanate, orthotolylene diisocyanate, and m-xylene diisocyanate.

The heat resistant porous layer may further contain a filler.

The filler is, for example, organic powder, inorganic powder or mixture thereof. The filler has preferably an average particle diameter of not less than 0.01 μm and not more than 1 μm. The filler is in the form of approximate sphere, plate, pillar, needle, whisker, fiber or the like, preferably approximate sphere to form uniform pores easily.

Examples of the organic powder as the filler include powders made of organic substances such as homopolymers of styrene, vinyl ketone, acrylonitrile, methyl methacrylate, ethyl methacrylate, glycidyl methacrylate, glycidyl acrylate, or methyl acrylate; copolymers of two or more of them; fluorine resins such as polytetrafluoroethylene, ethylene tetrafluoride-propylene hexafluoride copolymer, ethylene tetrafluoride-ethylene copolymer, and polyvinylidene fluoride; melamine resins; urea resins; polyolefins; and polymethacrylates. These organic powders may be used singly or in combination with another or more. Of these organic powders, a powder made of polytetrafluoroethylene is preferable from the standpoint of chemical stability.

Examples of the inorganic powder as the filler include powders made of inorganic substances such as metal oxides, metal nitrides, metal carbides, metal hydroxides, carbonates, and sulfates, and specific examples thereof include powders made of alumina, silica, titanium dioxide, and calcium carbonate. The inorganic powders may be used singly or in combination with another or more. Of these inorganic powders, an alumina powder is preferable from the standpoint of chemical stability. It is more preferable that all particles constituting the filler are alumina particles, and it is more preferable that all particles constituting the filler are alumina particles and a part or all of the alumina particles are in the form of approximate sphere.

The filler content in the heat resistant porous layer varies depending on the specific gravity of the material of the filler, and for example, when all particles constituting the filler are alumina particles, the weight of the filler is usually not less than 20 parts by weight and not more than 95 parts by weight, preferably not less than 30 parts by weight and not more than 90 parts by weight with respect to 100 parts by weight of the heat resistant porous layer. These ranges can be appropriately set depending on the specific gravity of the material of the filler.

In the laminated porous film, the porous film comprises a thermoplastic resin. The porous film has a thickness of usually from 3 to 30 μm, preferably from 3 to 20 μm. The porous film has fine pores and the size of the pore is usually not more than 3 μm, preferably not more than 1 μm, like the heat resistant porous layer. The porous film has a porosity of usually from 30 to 80 vol %, preferably from 40 to 70 vol %. In a non-aqueous electrolyte secondary battery, when the temperature thereof is over the usual use temperature, the porous film plays a role of occluding fine pores by softening of the thermoplastic resin constituting the porous film.

As the thermoplastic resin contained in the porous film, resins which soften at 80 to 180° C. and are indissoluble in an electrolytic liquid of the non-aqueous electrolyte secondary battery can be selected. Examples of the thermoplastic resin include polyolefins such as polyethylene, and polypropylene, and thermoplastic polyurethanes. These may be used also in combination with another or more. For softening at lower temperature to provide a shut down function, it is preferable that the thermoplastic resin is polyethylene. Examples of the polyethylene include polyethylenes such as low density polyethylene, high density polyethylene, linear polyethylene, and ultra high molecular weight polyethylene. For further enhancing the piercing strength of the porous film, the thermoplastic resin preferably contains ultra high molecular weight polyethylene. From the standpoint of production of the porous film, it is preferable in some cases that the thermoplastic resin contains a wax composed of a polyolefin of low molecular weight (weight-average molecular weight is not more than 10000).

The electrolytic liquid contains an electrolyte and an organic solvent.

Examples of the electrolyte in the electrolytic liquid include lithium salts such as $LiClO_4$, $LiPF_6$, $LiAsF_6$, $LiSbF_6$, $LiBF_4$, $LiCF_3SO_3$, $LiN(SO_2CF_3)_2$, $LiC(SO_2CF_3)_3$, $Li_2B_{10}Cl_{10}$, lower aliphatic carboxylic acid lithium salts, $LiAlCl_4$, and mixtures of two or more of them. Usually, it is preferable to use those containing at least one salt selected from the group consisting of $LiPF_6$, $LiAsF_6$, $LiSbF_6$, $LiBF_4$, $LiCF_3SO_3$, $LiN(SO_2CF_3)_2$ and $LiC(SO_2CF_3)_3$ containing fluorine as the lithium salt, among the lithium salts.

Examples of the organic solvent in the electrolytic liquid include carbonates such as propylene carbonate, ethylene carbonate, dimethyl carbonate, diethyl carbonate, ethyl methyl carbonate, 4-trifluoromethyl-1,3-dioxolan-2-one, and 1,2-di(methoxycarbonyloxy)ethane; ethers such as 1,2-dimethoxyethane, 1,3-dimethoxypropane, pentafluoropropyl methyl ether, 2,2,3,3-tetrafluoropropyl difluoromethyl ether, tetrahydrofuran, and 2-methyltetrahydrofuran; esters such as methyl formate, methyl acetate, and γ-butyrolactone; nitriles such as acetonitrile, and butyronitrile; amides such as N,N-dimethylformamide, and N,N-dimethylacetamide; carbamates such as 3-methyl-2-oxazoline; sulfur-containing compounds such as sulfolane, dimethyl sulfoxide, and 1,3-propane sultone; those obtained by introducing a fluorine substituent into these organic solvents. Usually, these organic solvents can be used in combination with another or more. Of them, mixed solvents containing carbonates are preferable, and more preferable are mixed solvents composed of a cyclic carbonate and a non-cyclic carbonate, or mixed solvents composed of a cyclic carbonate and an ether. Preferable examples of the mixed solvent composed of a cyclic carbonate and a non-cyclic carbonate include mixed solvents containing ethylene carbonate, dimethyl carbonate and ethyl methyl carbonate since these solvents have a broad operational temperature range, an excellent anode property, and is hard to be decomposed in even use of a graphite material such as natural graphite, and artificial graphite as the anode active material. From the standpoint of obtaining a particularly excellent safety improvement effect, lithium salts containing fluorine such as $LiPF_6$ and organic solvents having a fluorine substituent are more preferable. Mixed solvents containing dimethyl carbonate and ethers having a fluorine substituent such as pentafluoropropyl methyl ether, and 2,2,3,3-tetrafluoropropyl difluoromethyl ether are further preferable to be excellent also in a large current discharge property.

Instead of the electrolytic liquid, a solid electrolyte may be used. As the solid electrolyte, for example, polymer electrolytes can be used such as polymer compounds of polyethylene oxide type, polymer compounds containing a polyorganosiloxane chain and/or polyoxyalkylene chain. So-called gel type electrolytes obtained by allowing a polymer compound to keep a non-aqueous electrolyte solution can also be used. Safety can be further enhanced in some cases when a sulfide electrolyte such as $Li_2S$—$SiS_2$, $Li_2S$—$GeS_2$, $Li_2S$—$P_2S_5$, and $Li_2S$—$B_2S_3$, or an inorganic compound electrolyte containing a sulfide such as $Li_2S$—$SiS_2$—$Li_3PO_4$, and $Li_2S$—$SiS_2$—$Li_2SO_4$ is used. When a solid electrolyte is used in the non-aqueous electrolyte secondary battery of the present invention, the solid electrolyte plays a role of a separator in some cases. In this case, the separator is not required in some cases.

Next, the present invention will be illustrated further in detail by examples. Evaluation of a lithium mixed metal oxide (cathode active material) and a charge and discharge test thereof were carried out as described below.

1. Charge and Discharge Test

To a mixture of a cathode active material and an electrical conductive material acetylene black was added a N-methyl-2-pyrrolidone (hereinafter, referred to as NMP in some cases) solution of PVdF as a binder so as to give a composition of active material:electrical conductive material:binder=86:10:4 (weight ratio) and the mixture was kneaded to give a paste, the paste was applied on a #200 stainless steel mesh as a power collector and subjected to vacuum drying at 150° C. for 8 hours to obtain a cathode.

The resultant cathode was combined with a solution (hereinafter, described as $LiPF_6$/EC+EMC in some cases) obtained by dissolving $LiPF_6$ at a ratio of 1 mol/1 liter into a 50:50 (volume ratio) mixed liquid of ethylene carbonate (hereinafter, referred to as EC in some cases) and ethyl methyl carbonate (hereinafter, referred to as EMC in some cases) as an electrolytic liquid, a polypropylene porous membrane as a separator, and metal lithium as an anode, to fabricate a flat plate type battery.

Using the flat plate type battery, a charge and discharge test including charging at constant current and constant voltage and discharging at constant current was carried out under the following charge and discharge condition 1 and charge and discharge condition 2 while maintaining at 60° C. The cycle of the charge and discharge test was repeated, the discharge capacity after given number of cycles was measured, and the capacity retention was calculated according to the following equation.

<Charge and Discharge Condition 1>
 Charge maximum voltage: 4.3 V,
 Charge time: 8 hours,
 Charge current: 0.4 mA/cm$^2$,
 Discharge minimum voltage: 3.0 V,
 Dicharge current: 0.4 mA/cm$^2$
<Charge and Discharge Condition 2>
In 1-st Cycle, 2-nd Cycle
 Charge maximum voltage: 4.5 V,
 Charge time: 8 hours,
 Charge current: 0.6 mA/cm$^2$,
 Discharge minimum voltage: 3.0 V,
 Dicharge current: 0.6 mA/cm$^2$
In Third Cycle or Later
 Charge maximum voltage: 4.3 V,
 Charge time: 8 hours,
 Charge current: 0.6 mA/cm$^2$,
 Discharge minimum voltage: 3.0 V,
 Discharge current: 0.6 mA/cm$^2$ <Capacity Retention>

Capacity retention(%)=discharge capacity after given number of cycles/initial discharge capacity×100

2. Measurement and Analysis of EXAFS Spectrum of Lithium Mixed Metal Oxide

Measurement of the X-ray absorption spectrum at K absorption edge of Mn of a lithium mixed metal oxide was carried out using an XAFS measurement apparatus of a beam line 9A (BL-9A) in High Energy Accelerator Research Organization, Institute of Materials Structure Science, Photon Factory. Detuning of 60% was carried out for removal of higher-order light, using a Si (111) two crystal spectrometer. The incident X-ray intensity ($I_0$) was measured under normal temperature using a 17 cm ion chamber using $N_2$ (30 vol %)+He (70 vol %) as a gas, and the transmitted X-ray intensity ($I_1$) was measured under normal temperature using a 31 cm ion chamber using $N_2$ as a gas. The range of the energy measured, the interval thereof, and the accumulated time per one measurement point were measured as described below.

Accumulated for 1 second for each one point at an interval of 6.43 eV in a zone of an incident X-ray energy (E) of from 6040 eV to 6490 eV (measurement score is 70).

Accumulated for 1 second for each one point at an interval of 1 eV in a zone of an incident X-ray energy (E) of from 6490 eV to 6640 eV (measurement score is 150).

Accumulated for 2 seconds for each one point at an interval of 2.5 eV in a zone of an incident X-ray energy (E) of from 6640 eV to 7040 eV (measurement score is 160).

Accumulated for 2 seconds for each one point at an interval of 6 eV in a zone of an incident X-ray energy (E) of from 7040 eV to 7640 eV (measurement score is 101).

Correction of the energy was carried out by using metal copper as a standard sample, at an angle of the spectral crystal of 12.7185 degree at a pre-edge peak (about 8980 eV) of the spectrum of the X-ray absorption near-edge structure (XANES) at K absorption edge thereof.

According to the above descriptions, $I_0$ and $I_1$ were measured at each incident X-ray energy (E, x axis), and the X-ray absorbance (y axis) thereof was calculated according to the following equation, and the values were plotted on x axis-y axis, to obtain an X-ray absorption spectrum.

$$X\text{-ray absorbance } \mu t = -\ln(I_1/I_0)$$

Analysis of the EXAFS spectrum was carried out as described below.

From the X-ray absorption spectrum, an EXAFS spectrum at K absorption edge of Mn was obtained as described below, to obtain a radial distribution function. Specifically, analysis of the X-ray absorption spectrum obtained as describe above was carried out using an analysis software (REX2000 available from Rigaku Corporation). The energy $E_0$ (x axis) at K absorption edge of Mn was an energy value (x axis) at which its one-stage differential coefficient was maximum in a spectrum around K-absorption edge of Mn in the X-ray absorption spectrum. The background of the spectrum was determined by applying the Victoreen equation ($A\lambda^3 - B\lambda^4 + C$; $\lambda$ represents a wavelength of incident X-ray, and A, B and C are arbitrary constants) according to the least square method into a spectrum in a zone of lower energy than the K absorption edge of Mn described above, and the background was subtracted from the spectrum. Subsequently, for the spectrum, the absorbance ($\mu_0$) of an isolated atom was estimated by the Spline Smoothing method, and the EXAFS function $\chi(k)$ was extracted. k means the wave number of a photoelectron defined by $0.5123 \times (E-E_0)^{1/2}$, and the unit of k in this case was Å$^{-1}$. Finally, for the EXAFS function $k^3\chi(k)$ weighed with $k^3$, the Fourier transformation was carried out in the range of k of from 2.4 to 16.1 Å$^{-1}$ to obtain a radial distribution function, unless otherwise stated.

3. Measurement of BET Specific Surface Area of Lithium Mixed Metal Oxide

One g of a powder was dried in a nitrogen atmosphere at 150° C. for 15 minutes, then, the BET specific surface area was measured using FlowSorb II2300 manufactured by Mictomeritics.

4. Analysis of Composition of Lithium Mixed Metal Oxide

A powder was dissolved in hydrochloric acid, then, the composition thereof was measured by the inductively coupled plasma atomic emission spectrometry (hereinafter, referred to as ICP-AES in some cases) using SPS 3000 manufactured by Seiko Instruments Inc.

5. Measurement of Powder X-Ray Diffraction of Lithium Mixed Metal Oxide

Measurement of powder X-ray diffraction of a lithium mixed metal oxide was carried out using RINT 2500 TTR type manufactured by Rigaku Corporation. A lithium mixed metal oxide was filled in a dedicated substrate, and the measurement was carried out in the range of diffraction angle 2θ=10° to 90° using a CuKα radiation source, to obtain a powder X-ray diffraction pattern. The Rietveld analysis was carried out according to an analysis program RIETAN-2000 (see, F. Izumi and T. Ikeda, Mater. Sci. Forum, 321-324 (2000) 198), and the space group of the crystal structure of the lithium mixed metal oxide was confirmed.

Comparative Example 1

1. Production of Lithium Mixed Metal Oxide

In a titanium beaker, 50 g of lithium hydroxide monohydrate, 500 ml of distilled water and 200 ml of ethanol were stirred to completely dissolve the lithium hydroxide monohydrate, to prepare a lithium hydroxide aqueous solution. The titanium beaker containing the lithium hydroxide aqueous solution was allowed to stand still in a lower constant temperature vessel and kept at −10° C. In a glass beaker, 23.17 g of nickel(II) chloride hexahydrate, 23.25 g of manganese(II) chloride tetrahydrate, 7.28 g of cobalt(II) nitrate hexahydrate (the molar ratio of Ni:Mn:Co=0.41:0.49:0.10) and 500 ml of distilled water were stirred to completely dissolve the nickel (II) chloride hexahydrate, manganese(II) chloride tetrahydrate and cobalt(II) nitrate hexahydrate to obtain a nickel-manganese-cobalt aqueous solution. The aqueous solution was dropped into the lithium hydroxide aqueous solution kept at −10° C., to form a precipitate.

The mixed liquid containing the precipitate was removed from the lower constant temperature vessel, and an operation of blowing air (bubbling) was conducted for 1 day at room temperature. The mixed liquid after bubbling was subjected to filtration and washing with distilled water to obtain a precipitate.

In a polytetrafluoroethylene beaker, 50 g of lithium hydroxide monohydrate, 50 g of potassium chlorate, 309 g of potassium hydroxide and 500 ml of distilled water were stirred, and the precipitate obtained above was added, and the mixture was further stirred to disperse the precipitate, obtaining a liquid mixture.

The polytetrafluoroethylene beaker containing the liquid mixture was allowed to stand still in an autoclave, and subjected to a hydrothermal treatment at a temperature of 220° C. for 5 hours, and cooled naturally, to obtain a hydrothermally treated article. The hydrothermally treated article was removed from the autoclave, and decantation was carried out with distilled water to obtain a washed article.

The washed article was mixed with a lithium hydroxide aqueous solution prepared by dissolving 10.49 g of lithium hydroxide monohydrate into 100 ml of distilled water, and dried at 100° C. to obtain a mixture. The mixture was ground using an agate mortar to obtain a powder which was then placed in an alumina calcination vessel, and calcination thereof was carried out for 6 hours in air at 800° C. using an electric furnace. The calcined article was cooled down to room temperature, ground and washed with distilled water by decantation, and filtrated and dried at 100° C. for 8 hours to obtain a powder $A_1$.

The composition of the powder $A_1$ was analyzed to resultantly find that the molar ratio of Li:Ni:Mn:Co was 1.34:0.41:0.49:0.10. The BET specific surface area of $A_1$ was 6.4 m$^2$/g.

The powder X-ray diffraction of the powder $A_1$ was measured, to find a compound of layered structure. As a result of the Rietveld analysis, the crystal structure of $A_1$ was hexagonal belonging to a space group R-3m. The powder X-ray diffraction pattern is shown in FIG. 1.

For the powder $A_1$, the EXAFS spectrum at K absorption edge of Mn was obtained and the Fourier transformation was carried out to obtain a radial distribution function, as described above. In the radial distribution function, the intensity ratio $I_B/I_A$ of the peak A at 1.50 Å and the peak B at 2.49 Å was 0.95.

2. Charge and Discharge Test of Lithium Secondary Battery Under Charge and Discharge Condition 1

Using the powder $A_1$, a flat plate battery was fabricated, and the cycle of a charge and discharge test was repeated, as a result, the capacity retention (%) at 1-st cycle, 10-th cycle, 20-th cycle and 30-th cycle were 100, 117, 136 and 149, respectively.

3. Charge and Discharge Test of Lithium Secondary Battery Under Charge and Discharge Condition 2

Using the powder $A_1$, a flat plate battery was fabricated, and the cycle of a charge and discharge test was repeated, as a result, the capacity retention (%) at 1-st cycle, 3-rd cycle, 5-th cycle and 10-th cycle were 100, 108, 108 and 108, respectively.

Example 1

1. Production of Lithium Mixed Metal Oxide

The washed article obtained in Comparative Example 1 was filtrated and washed with distilled water, and the resultant solid component was dried at 100° C., to obtain a dried article. Then, 2.0 g of the dried article and 1.79 g of lithium hydroxide monohydrate were mixed and ground under dry condition using an agate mortar to obtain a mixture which was then placed in an alumina calcination vessel, and calcination thereof was carried out for 6 hours in air at 800° C. using an electric furnace. The calcined article was cooled down to room temperature, ground and washed with distilled water by decantation, and filtrated and dried at 100° C. for 8 hours, to obtain a powder $B_1$.

The composition of the powder $B_1$ was analyzed to resultantly find that the molar ratio of Li:Ni:Mn:Co was 1.55:0.40:0.50:0.10. The BET specific surface area of $B_1$ was 4.0 m$^2$/g.

The powder X-ray diffraction of the powder $B_1$ was measured, to find a compound of layered structure. As a result of the Rietveld analysis, the crystal structure of $B_1$ was hexagonal belonging to a space group R-3m. The powder X-ray diffraction pattern is shown in FIG. 1.

For the powder $B_1$, the EXAFS spectrum at K absorption edge of Mn was obtained and the Fourier transformation was carried out to obtain a radial distribution function, as described above. In the radial distribution function, the intensity ratio $I_B/I_A$ of the peak A at 1.53 Å and the peak B at 2.49 Å was 0.83.

2. Charge and Discharge Test of Lithium Secondary Battery Under Charge and Discharge Condition 1

Using the powder $B_1$, a flat plate battery was fabricated, and the cycle of a charge and discharge test was repeated, as a result, the capacity retention (%) at 1-st cycle, 10-th cycle, 20-th cycle and 30-th cycle were 100, 134, 173 and 194, respectively, that is, these were higher than the capacity retention of $A_1$. The discharge capacity (mAh/g) at 30-th cycle was 182, being an extremely higher value.

3. Charge and Discharge Test of Lithium Secondary Battery Under Charge and Discharge Condition 2

Using the powder $B_1$, a flat plate battery was fabricated, and the cycle of a charge and discharge test was repeated, as a result, the capacity retention (%) at 1-st cycle, 3-rd cycle, 5-th cycle and 10-th cycle were 100, 131, 132 and 132, respectively, that is, these were higher than the capacity retention of $A_1$. The discharge capacity (mAh/g) at 10-th cycle was 204, being an extremely higher value.

Example 2

1. Production of Lithium Mixed Metal Oxide

The same procedure as in Example 1 was carried out to obtain a powder $B_2$ excepting that 2.0 g of the dried article in Example 1 and 3.58 g of lithium hydroxide monohydrate were mixed and ground under dry condition using an agate mortar.

The composition of the powder $B_2$ was analyzed to resultantly find that the molar ratio of Li:Ni:Mn:Co was 1.57:0.40:0.49:0.11. The BET specific surface area of $B_2$ was 3.8 m²/g.

The powder X-ray diffraction of the powder $B_2$ was measured, to find a compound of layered structure. As a result of the Rietveld analysis, the crystal structure of $B_2$ was hexagonal belonging to a space group R-3m. The powder X-ray diffraction pattern is shown in FIG. 1.

For the powder $B_2$, the EXAFS spectrum at K absorption edge of Mn was obtained and the Fourier transformation was carried out to obtain a radial distribution function, as described above. In the radial distribution function, the intensity ratio $I_B/I_A$ of the peak A at 1.53 Å and the peak B at 2.49 Å was 0.81.

2. Charge and Discharge Test of Lithium Secondary Battery Under Charge and Discharge Condition 1

Using the powder $B_2$, a flat plate battery was fabricated, and the cycle of a charge and discharge test was repeated, as a result, the capacity retention (%) at 1-st cycle, 10-th cycle, 20-th cycle and 30-th cycle were 100, 123, 153 and 179, respectively, that is, these were higher than the capacity retention of $A_1$.

3. Charge and Discharge Test of Lithium Secondary Battery Under Charge and Discharge Condition 2

Using the powder $B_2$, a flat plate battery was fabricated, and the cycle of a charge and discharge test was repeated, as a result, the capacity retention (%) at 1-st cycle, 3-rd cycle, 5-th cycle and 10-th cycle were 100, 136, 136 and 136, respectively, that is, these were higher than the capacity retention of $A_1$.

Example 3

1. Production of Lithium Mixed Metal Oxide

In a polypropylene beaker, 30.21 g of lithium hydroxide was added into 300 ml of distilled water and the mixture was stirred to completely dissolve lithium hydroxide, to prepare a lithium hydroxide aqueous solution. In a glass beaker, 13.90 g of nickel(II) chloride hexahydrate, 13.95 g of manganese (II) chloride tetrahydrate and 4.05 g of iron(III) chloride hexahydrate (the molar ratio of Ni:Mn:Fe=0.41:0.49:0.1) and 300 ml of distilled water were stirred to completely dissolve nickel(II) chloride hexahydrate, manganese(II) chloride tetrahydrate and iron(III) chloride hexahydrate, to obtain a nickel-manganese-iron aqueous solution. The nickel-manganese-iron aqueous solution was dropped while stirring the potassium hydroxide aqueous solution to from a precipitate.

Then, the mixed liquid containing the generated precipitate was subjected to a bubbling operation at room temperature for 1 day in the same manner as in Comparative Example 1. The mixed liquid after bubbling was subjected to filtration and washing with distilled water, to obtain a precipitate.

In a polytetrafluoroethylene beaker, 30 g of lithium hydroxide monohydrate, 29 g of potassium chlorate, 185 g of potassium hydroxide and 500 ml of distilled water were stirred, and the precipitate obtained above was added, and the mixture was further stirred to disperse the precipitate, obtaining a liquid mixture.

The polytetrafluoroethylene beaker containing the liquid mixture was allowed to stand still in an autoclave, and subjected to a hydrothermal treatment at a temperature of 220° C. for 5 hours, and cooled naturally, to obtain a hydrothermally treated article. The hydrothermally treated article was removed from the autoclave, and decantation was carried out with distilled water, to obtain a washed article.

The solid component obtained from the washed article was dried at 100° C., to obtain a dried article. Then, 2.0 g of the dried article and 1.79 g of lithium hydroxide monohydrate were mixed and ground under dry condition using an agate mortar to obtain a mixture which was then placed in an alumina calcination vessel, and calcination thereof was carried out for 6 hours in air at 800° C. using an electric furnace. The calcined article was cooled down to room temperature, ground and washed with distilled water by decantation, and filtrated and dried at 100° C. for 8 hours, to obtain a powder $B_3$.

The composition of the powder $B_3$ was analyzed to resultantly find that the molar ratio of Li:Ni:Mn:Fe was 1.42:0.40:0.50:0.1. The BET specific surface area of $B_3$ was 5.1 m²/g.

The powder X-ray diffraction of the powder $B_3$ was measured, to find a compound of layered structure. As a result of the Rietveld analysis, the crystal structure of $B_3$ was hexagonal belonging to a space group R-3m. The powder X-ray diffraction pattern is shown in FIG. 1.

For the powder $B_3$, the EXAFS spectrum at K absorption edge of Mn was obtained and the Fourier transformation was carried out to obtain a radial distribution function, as described above. In the radial distribution function, the intensity ratio $I_B/I_A$ of the peak A at 1.44 Å and the peak B at 2.41 Å was 0.87. In the case of inclusion of Fe as in Example 3, for the EXAFS function $k^3\chi(k)$, the Fourier transformation was carried out in the range of k of from 2.4 to 10.65 Å$^{-1}$ to obtain a radial distribution function.

2. Charge and Discharge Test of Lithium Secondary Battery Under Charge and Discharge Condition 1

Using the powder $B_3$, a flat plate battery was fabricated, and the cycle of a charge and discharge test was repeated, as a result, the capacity retention (%) at 1-st cycle, 10-th cycle, 20-th cycle and 30-th cycle were 100, 162, 196 and 201, respectively, that is, these were higher than the capacity retention of $A_1$. The discharge capacity (mAh/g) at 30-th cycle was 182, being an extremely higher value.

3. Charge and Discharge Test of Lithium Secondary Battery Under Charge and Discharge Condition 2

Using the powder $B_3$, a flat plate battery was fabricated, and the cycle of a charge and discharge test was repeated, as a result, the capacity retention (%) at 1-st cycle, 3-rd cycle, 5-th cycle and 10-th cycle were 100, 144, 141 and 141, respectively, that is, these were higher than the capacity retention of $A_1$. The discharge capacity (mAh/g) at 10-th cycle was 176, being an extremely higher value.

Production Example 1

Production of Laminated Porous Film (1) Production of Coating Liquid in the Form of Slurry for Heat Resistant Porous Layer 272.7 g of calcium chloride was dissolved in 4200 g of NMP, then, 132.9 g of para-phenylenediamine was added and dissolved completely. To the resultant solution was added 243.3 g of terephthalic dichloride gradually and polymerization was conducted to obtain a para-aramide which was then further diluted with NMP to obtain a para-aramide solution having a concentration of 2.0 wt %. To 100 g of the resultant para-aramide solution was added 2 g of an alumina powder (a) (manufactured by Nippon Aerosil Co., Ltd., alumina C, average particle diameter: 0.02 μm) and 2 g of an alumina powder (b) (manufactured by Sumitomo Chemical Co., Ltd., Sumikorandom, AA03, average particle diameter: 0.3 μm) as a filler in a total amount of 4 g and these were mixed and treated three times by a nanomizer, further, filtrated through a 1000 mesh woven wire, and de-foamed under reduced pressure, to produce a coating liquid in the form of slurry for heat resistant porous layer. The weight of the alumina powder (filler) with respect to the total weight of the para-aramide and alumina powder was 67 wt %.

(2) Production of Laminated Porous Film

As the porous film, a polyethylene porous membrane (thickness: 12 μm, air permeability: 140 sec/100 cc, average pore size: 0.1 μm, gap ratio: 50%) was used. the polyethylene porous membrane was fixed on a PET film having a thickness of 100 μm, and the porous membrane was coated with the coating liquid in the form of slurry for heat resistant porous layer by a bar coater manufactured by Tester Sangyo Co., Ltd. the PET film coated with the porous membrane was immersed in water as a poor solvent while keeping integration thereof, to precipitate a para-aramide porous membrane (heat resistant porous layer), then, the solvent was dried, and peeled from the PET film to obtain a laminated porous film in which the heat resistant porous layer and the porous film are laminated.

(3) Evaluation of Laminated Porous Film

The laminated porous film had a thickness of 16 μm, and the para-aramide porous membrane (heat resistant porous layer) had a thickness of 4 μm. The laminated porous film had an air permeability of 180 sec/100 cc and a gap ratio of 50%. The cross-section of the heat resistant porous layer of the laminated porous film was observed by a scanning electron microscope (SEM) to find relatively small fine pores of about 0.03 μm to 0.06 μm and relatively large fine pores of about 0.1 μm to 1 μm.

Evaluations of the laminated porous film were carried out according to the following (A) to (C)

(A) Measurement of Thickness

The thickness of the laminated porous film and the thickness of the porous film were measured according to JIS K7130-1992. As the thickness of the heat resistant porous layer, a value obtained by subtracting the thickness of the porous film from the thickness of the laminated porous film was used.

(B) Measurement of Air Permeability by Gurley Method

The air permeability of the laminated porous film was measured according to JIS P8117 by a Gurley Densometer of digital timer mode manufactured by Yasuda Seiki Seisakusho Ltd.

(C) Porosity

A sample of the laminated porous film was cut into a square having a length of one side of 10 cm, and the weight W (g) and the thickness D (cm) thereof were measured. The weight (Wi) of each layer in the sample was measured, and from Wi and the true specific gravity (g/cm$^2$) of the material of each layer, the volume of each layer was calculated, and the porosity (vol %) was calculated according to the following equation.

Porosity(vol %)=100×{1−($W1$/true specific gravity 1+$W2$/true specific gravity 2+ . . . +$Wn$/true specific gravity $n$)/(10×10×$D$)}

In the examples, when the laminated porous film obtained in Production Example 1 is used as the separator, a lithium secondary battery with further enhanced thermal membrane breakage temperature can be obtained.

INDUSTRIAL APPLICABILITY

According to the present invention, a non-aqueous electrolyte secondary battery with capacity retention improved as compared with conventional lithium secondary batteries can be obtained. Thus obtained non-aqueous electrolyte secondary battery is extremely useful, particularly, as a non-aqueous electrolyte secondary battery which is required to show high output under high current rate, that is, as a non-aqueous electrolyte secondary battery for automobiles and power tools such as electric tools.

The invention claimed is:

1. A lithium mixed metal oxide containing Li, Mn and M (M represents at least one metal element, and is free from Li or Mn) with the amount (mol) of Li being not less than 1.4 and not more than 1.8 with respect to the total amount (mol) of Mn and M, and having a peak around 1.5 Å (peak A), a peak around 2.5 Å (peak B), and the value of $I_B/I_A$ is not less than 0.15 and not more than 0.9 in a radial distribution function obtained by subjecting an extended X-ray absorption fine structure (EXAFS) spectrum at K absorption edge of Mn in the oxide to the Fourier transformation, wherein $I_A$ is the intensity of peak A and $I_B$ is the intensity of peak B.

2. The lithium mixed metal oxide according to claim 1, wherein M represents Co and/or Ni.

3. The lithium mixed metal oxide according to claim 1, wherein the lithium mixed metal oxide has a layered crystal structure.

4. The lithium mixed metal oxide according to claim 1, wherein the amount (mol) of Mn is not less than 0.4 and not more than 1 with respect to the total amount (mol) of Mn and M.

5. A cathode active material for non-aqueous electrolyte secondary battery comprising the lithium mixed metal oxide according to claim 1.

6. A cathode for non-aqueous electrolyte secondary battery comprising the cathode active material for non-aqueous electrolyte secondary battery according to claim 5.

7. A non-aqueous electrolyte secondary battery comprising the cathode for non-aqueous electrolyte secondary battery according to claim 6.

8. The non-aqueous electrolyte secondary battery according to claim 7, further comprising a separator.

9. The non-aqueous electrolyte secondary battery according to claim 8, wherein the separator is a separator composed of a laminated porous film obtained by laminating a heat resistant porous layer containing a heat resistant resin and a porous film containing a thermoplastic resin.

* * * * *